(12) United States Patent
Hayano

(10) Patent No.: US 9,701,701 B2
(45) Date of Patent: Jul. 11, 2017

(54) TRANSITION METAL CARBENE COMPLEX AND METHOD OF PRODUCING THE SAME

(71) Applicant: ZEON CORPORATION, Tokyo (JP)

(72) Inventor: Shigetaka Hayano, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/905,479

(22) PCT Filed: Jul. 17, 2014

(86) PCT No.: PCT/JP2014/003812
§ 371 (c)(1),
(2) Date: Jan. 15, 2016

(87) PCT Pub. No.: WO2015/008493
PCT Pub. Date: Jan. 22, 2015

(65) Prior Publication Data
US 2016/0152645 A1    Jun. 2, 2016

(30) Foreign Application Priority Data
Jul. 17, 2013  (JP) ................................. 2013-148881

(51) Int. Cl.
*C07F 11/00* (2006.01)
*C08F 4/78* (2006.01)

(52) U.S. Cl.
CPC ............... *C07F 11/00* (2013.01); *C08F 4/78* (2013.01)

(58) Field of Classification Search
CPC ....................................................... C07F 11/00
USPC .......................................................... 556/58
See application file for complete search history.

(56) References Cited

U.S. PATENT DOCUMENTS

| 7,365,140 B2 * | 4/2008 | Piers | .................... | B01J 31/2265 |
| | | | | 502/155 |
| 2006/0128912 A1 | 6/2006 | Piers et al. | | |
| 2011/0098497 A1 * | 4/2011 | Chahen et al. | | |

FOREIGN PATENT DOCUMENTS

| JP | 2002-504487 A | 2/2002 |
| WO | 99/42469 A1 | 8/1999 |
| WO | 2008-501731 A | 1/2008 |

OTHER PUBLICATIONS

Tonzeit et al., Organometallics 2006, 25, 4301-4306. From ISR on record.*
Jan et al., J Organometallic Chem 696 (2011) 4079-4089. From ISR on record.*
International Search Report dated Oct. 14, 2014, issued in counterpart Application No. PCT/JP2014/003812 (2 pages).
Extended European Search Report dated Jan. 16, 2017, issued in Application No. EP14827072 (6 pages).
Muhammad T. Jan, et.al., "Synthesis and characterization of a trianionic pincer supported Mo-alkylidene anion and alkyne insertion into a Mo(IV)-Cpincer bond to form metallocyclopropene(η2-vinyl)complexes", Journal of Organometallic Chemistry, Jun. 2011, vol. 696, pp. 4079-4089 (11 pages).
Tonzetich Z. J., et. al., Reaction of Phosphoranes with Mo(N-2,6-i-Pr2C6H3) (CHCMe3)[OCMe(CF3)2]2: Synthesis and Reactivity of an Anionic Imido Alkylidyne Complex, Jan. 2006, vol. 25, pp. 4301-4306 (6 pages).

* cited by examiner

*Primary Examiner* — Fereydoun G Sajjadi
*Assistant Examiner* — Kofi Adzamli
(74) *Attorney, Agent, or Firm* — Westerman, Hattori, Daniels & Adrian, LLP

(57) ABSTRACT

Provided are a transition metal carbene complex represented by the following general formula (1) and a method of producing the same. (In general formula (1), M represents for example a molybdenum atom, $R^1$ represents for example a $C_1$-$C_{20}$ alkyl group optionally having a substituent, $L^1$ to $L^3$ each represent a ligand selected for example from a halogen group, $R^2$ and $R^3$ each represent for example a hydrogen atom or a $C_1$-$C_{20}$ alkyl group optionally having a substituent. A represents for example a nitrogen atom, and $R^4$ to $R^7$ each represent for example a $C_1$-$C_{20}$ alkyl group optionally having a substituent.)

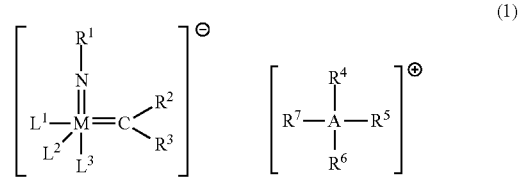

(1)

2 Claims, No Drawings

TRANSITION METAL CARBENE COMPLEX AND METHOD OF PRODUCING THE SAME

TECHNICAL FIELD

The disclosure relates to a transition metal carbene complex and a method of producing the same. More particularly, the disclosure relates to a transition metal carbene complex that is useful for example as a metathesis catalyst and is excellent in handleability, and a method of producing the same.

BACKGROUND

Transition metal carbene complexes, such as ruthenium carbene complexes called Grubbs' catalyst and molybdenum carbene complexes and tungsten carbene complexes called Schrock's catalyst, are known as highly-active catalysts for metathesis reactions (hereinafter frequently referred to as "metathesis catalyst") and are widely used.

Among the transition metal carbene complexes, molybdenum carbene complexes and tungsten carbene complexes exhibit extremely high activity as metathesis catalysts, and may promote metathesis reactions stereospecifically when the substituent and the ligand on the metal are suitably selected, as disclosed for example in JP2002504487A (PTL 1). Thus, various studies have been made on molybdenum carbene complexes and tungsten carbene complexes.

However, molybdenum carbene complexes and tungsten carbene complexes are less stable in air than ruthenium carbene complexes or the like. Thus, molybdenum carbene complexes and tungsten carbene complexes (hereinafter frequently referred to as "molybdenum carbene complexes, etc.") are not easy to handle (or are poor in handleability), which is a problem.

CITATION LIST

Patent Literature

PTL JP2002504487A

SUMMARY

Technical Problem

It is therefore an object of the disclosure to provide a transition metal carbene complex that is excellent in handleability for its higher stability in air than the conventional molybdenum carbene complex, etc. and is usable as a metathesis catalyst or the like similarly to the conventional molybdenum carbene complex, etc.

Solution to Problem

As a result of extensive studies made to achieve the above objects, the following facts have been discovered: When the conventional molybdenum carbene complex, etc. and an onium salt are mixed together in a solvent, the onium salt is incorporated into the structure of the carbene complex and a new complex is formed. Further, the complex as formed is more stable in an thin the original complex, while maintaining the activity as a metathesis catalyst. Based on these findings, the product and method disclosed herein have been reached.

Given the above, provided herein is a transition metal carbene complex represented by the following general formula (1).

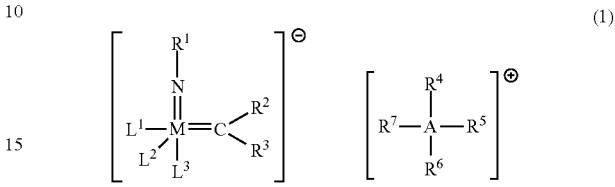

In general formula (1) above, M represents a molybdenum atom or a tungsten atom; $R^1$ represents a $C_1$-$C_{20}$ alkyl group optionally having a substituent or a $C_6$-$C_{20}$ aryl group optionally having a substituent; $L^1$, $L^2$, and $L^3$ each represent a ligand selected from a halogen group, an alkoxy group optionally having a substituent, and an aryloxy group optionally having a substituent, wherein $L^1$, $L^2$, and $L^3$ are the same as or different from one another, or at least two of $L^1$, $L^2$, and $L^3$ bind together to form a ring structure with M; $R^2$ and $R^3$ each represent a hydrogen atom, a $C_1$-$C_{20}$ alkyl group optionally having a substituent, or a $C_6$-$C_{20}$ aryl group optionally having a substituent, wherein $R^2$ and $R^3$ are the same as or different from each other; A represents a nitrogen atom or a phosphorus atom; and $R^4$, $R^5$, $R^6$, and $R^7$ each represent a $C_1$-$C_{20}$ alkyl group optionally having a substituent or a $C_6$-$C_{20}$ aryl group optionally having a substituent, wherein $R^4$, $R^5$, $R^6$, and $R^7$ are the same as or different from one another, or at least to of $R^4$, $R^5$, $R^6$, and $R^7$ bind together to form a ring structure with A.

Also provided herein is a method of producing the above-described transition metal carbene complex, comprising mixing together a transition metal carbene complex represented by the following general formula (2) and an onium salt represented by the following general formula (3) in a solvent.

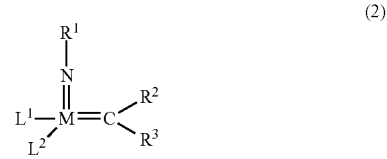

In general formula (2), M represents a molybdenum atom or a tungsten atom; $R^1$ represents a $C_1$-$C_{20}$ alkyl group optionally having a substituent or a $C_6$-$C_{20}$ aryl group optionally having a substituent; $L^1$ and $L^2$ each represent a ligand selected from a halogen group, an alkoxy group optionally having a substituent, and an aryloxy group optionally having a substituent, wherein $L^1$ and $L^2$ are the same as or different from each other, or $L^1$ and $L^2$ bind together to form a ring structure with M; and $R^2$ and $R^3$ each represent a hydrogen atom, a $C_1$-$C_{20}$ alkyl group optionally having a substituent, or a $C_6$-$C_{20}$ aryl group optionally having a substituent, wherein $R^2$ and $R^3$ are the same as or different from each other.

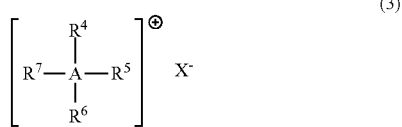

(3)

In general formula (3). A represents a nitrogen atom or a phosphorus atom; $R^4$, $R^5$, $R^6$, and $R^7$ each represent a $C_1$-$C_{20}$ alkyl group optionally having a substituent or a $C_6$-$C_{20}$ aryl group optionally having a substituent wherein $R^4$, $R^5$, $R^6$, and $R^7$ are the same as or different from one another, or at least two of $R^4$, $R^5$, $R^6$, and $R^7$ bind together to form a ring structure with A; and $X^-$ represents an anion selected from a halide ion, an alkoxide anion optionally having a substituent, and an aryloxide anion optionally having a substituent.

Advantageous Effect

According to the disclosure, provided is the transition metal carbene complex that is excellent in handleability for its higher stability in air than the conventional molybdenum carbene complex etc., and is usable as a metathesis catalyst or the like similarly to the conventional molybdenum carbene complex. etc.

DETAILED DESCRIPTION

The transition metal carbene complex of the disclosure is a transition metal carbene complex represented by the following general formula (1):

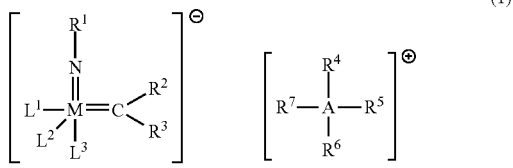

(1)

In general formula (1), M represents a molybdenum atom or a tungsten atom; $R^1$ represents a $C_1$-$C_{20}$ alkyl group optionally having a substituent (or a substituted or unsubstituted $C_1$-$C_{20}$ alkyl group) or a $C_6$-$C_{20}$ aryl group optionally having a substituent; $L^1$, $L^2$ and $L^3$ each represent a ligand selected from a halogen group, an alkoxy group optionally having substituent, and an aryloxy group optionally having a substituent; $R^2$ and $R^3$ each represent hydrogen atom, a $C_1$-$C_{20}$ alkyl group optionally having a substituent, or a $C_6$-$C_{20}$ aryl group optionally having a substituent; A represents a nitrogen atom or a phosphorus atom; $R^4$, $R^5 R^6$, and $R^7$ each represent a $C_1$-$C_{20}$ alkyl group optionally having a substituent or as $C_6$-$C_{20}$ aryl group optionally having a substituent.

In general formula (1), M represents a molybdenum atom or a tungsten atom, which is a central metal of the complex. The central metal of the disclosed transition metal carbene complex can be either a molybdenum atom or a tungsten atom.

In general formula (1) the group represented by $R^1$ or specifically the group on the nitrogen atom bound to the central-metal atom M of the complex, is a $C_1$-$C_{20}$ alkyl group optionally having a substituent or a $C_6$-$C_{20}$ aryl group optionally having a substituent. Specific examples of the $C_1$-$C_{20}$ alkyl group include, but are not limited to, a methyl group, an ethyl group, an isopropyl group, a t-butyl group, and a n-butyl group. Specific examples of the aryl group with a carbon number of 6 to 20 include, but are not limited to, a phenyl group, a 4-methylphenyl group, a 2,6-dimethylphenyl group, a 2,6-diisopropylphenyl group, and a mesityl group.

In general formula (1), the groups represented by $R^2$ and $R^3$, or specifically the groups on the carbene carbon atom, are each a hydrogen atom a $C_1$-$C_{20}$ alkyl group optionally having a substituent, or a $C_6$-$C_{20}$ aryl group optionally having a substituent. Specific examples of the $C_1$-$C_{20}$ alkyl group include, but are not limited to, a methyl group, an ethyl group, an isopropyl group, a t-butyl group, and a n-butyl group. One specific example of the $C_1$-$C_{20}$ alkyl group having a substituent is, but is not limited to, a 2-methyl-2-phenylethyl group. Further, specific examples of the aryl group with a carbon number of 6 to 20 include, but are not limited to, a phenyl group, a 4-methylphenyl group, a 2,6-dimethylphenyl group, a 2,6-diisopropylphenyl group, and a mesityl group. The groups represented by $R^2$ and $R^3$ may be the same groups as or different groups from each other.

In general formula (1), the ligands represented by $L^1$, $L^2$, and $L^3$ are ligands each of which is selected from a halogen group; an alkoxy group optionally having a substituent, and an aryloxy group optionally having a substituent. Here, the carbon number of the alkoxy group optionally having a substituent is preferably 1 to 30, and the carbon number of the aryloxy group optionally having a substituent is preferably 6 to 30. Specific examples of the halogen group include, but are not limited to, a chloro group, a bromo group, and an iodine group. Specific examples of the alkoxy group include, but are not limited to, a methoxy group, an ethoxy group, an isopropoxy group, a t-butoxy group, and a n-butoxy group. Further, specific examples of the alkoxy group having a substituent include, but are not limited to, a trifluoromethoxy group, a pentafluoroethoxy group, and a 1,1,1,3,3,3-hexafluoro-2-methyl-2-propoxy group. Specific examples of the aryloxy group include, but are not limited to, a phenoxy group, a 4-methylphenoxy group, a 2,6-dimethylphenoxy group, and a 2,6-diisopropylphenoxy group. Further, one example of the aryloxy group having a substituent is, but is not limited to, a pentafluorophenoxy group. The ligands represented by $L^1$, $L^2$, and $L^3$ may be the same ligands as or different ligands from one another, or at least two of $L^1$, $L^2$, and $L^3$ may bind together to form a ring structure with the central-metal atom M. Examples of the ligand formed when two of $L^1$, $L^2$, and $L^3$ bind together include, but are not limited to, a 2,2'-biphenoxy group and a 3,3'-di-t-butyl-5,5', 6,6'-tetramethyl-2,2'-biphenoxy group.

In general formula (1), A represents a nitrogen atom or a phosphorus atom. The atom represented by A coordinates to the molybdenum atom or the tungsten atom being the central metal of the complex to form part of the complex. The atom represented by A can be either a nitrogen atom or a phosphorus atom.

In general formula (1), $R^4$, $R^5$, $R^6$, and $R^7$ each represent a $C_1$-$C_{20}$ alkyl group optionally having a substituent or a $C_6$-$C_{20}$ aryl group optionally having a substituent. Specific examples of the $C_1$-$C_{20}$ alkyl group include, but are not limited to, a methyl group, an ethyl group, an isopropyl group, a t-butyl group, and a n-butyl group. Specific examples of the aryl group with a carbon number of 6 to 20 include, but are not limited to, a phenyl group, a 4-methylphenyl group, a 2,6-dimethylphenyl group, a 2,6-diisopropylphenyl group, and a mesityl group. The groups represented by $R^4$, $R^5$, $R^6$, and $R^7$ may be the same groups as or different groups from one another, or at least two of $R^4$, $R^5$, $R^6$, and $R^7$ may bind together to form a ring structure with the nitrogen atom or the phosphorus atom represented by A. Here, without particular limitation, if the atom represented by A is a nitrogen atom, the structure obtained when at least two of $R^4$, $R^5$, $R^6$, and $R^7$ bind together to form a ring with the nitrogen atom may be an imidazolium cation structure or a pyrrolidinium cation structure.

Although not limited in particular, a method of obtaining the transition metal carbene complex of the disclosure represented by general formula (1) can suitably provide the transition metal carbene complex of the disclosure, in accordance with the method of producing the transition metal carbene complex of the disclosure described below. Specifically, the method of producing the transition metal carbene complex of the disclosure achieves production of the transition metal carbene complex of the disclosure represented by general formula (1) above by mixing together a transition metal carbene complex represented by the following general formula (2) and an onium salt represented by the following general formula (3) in a solvent.

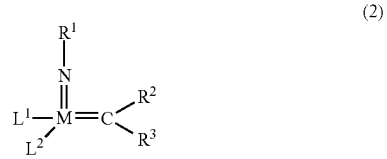

(2)

In general formula (2) M, $R^1$, $R^2$, $R^3$, $L^1$, and $L^2$ have the same meaning as M, $R^1$, $R^2$, $R^3$, $L^1$, and $L^2$ of general formula (1), respectively. As previously stated, the groups represented by $R^2$ and $R^3$ may be the same groups as or different groups from each other. The ligands represented by $L^1$ and $L^2$ may be the same ligands as or different ligands from each another, or $L^1$ and $L^2$ may bind together to form a ring structure with the central-metal atom M.

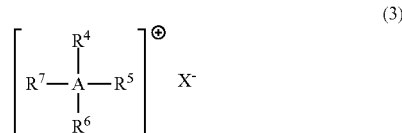

(3)

In general formula (3), A, $R^4$, $R^5$, $R^6$, and $R^7$ have the same meaning as A, $R^4$, $R^5$, $R^6$, and $R^7$ of general formula (1), respectively. As previously stated, the groups represented by $R^4$, $R^5$, $R^6$, and $R^7$ may be the same groups as or different groups from one another, or at least two of $R^4$, $R^5$, $R^6$, and $R^7$ may bind together to form a ring structure with the nitrogen atom or the phosphorus atom represented by A.

$X^-$ in general formula (3) represents an anion selected from a halide ion, an alkoxide anion optionally having a substituent, and an aryloxide anion optionally having a substituent. The anion represented by $X^-$ will become a ligand that coordinates to the central metal (i.e., a ligand represented by $L^3$ in general formula (1)) in the intended transition metal carbene complex of the disclosure. Specific examples thereof include anions corresponding to the groups given as examples of the ligand represented by $L^3$.

Specific examples of the onium salt represented by general formula include, but are not limited to, tetramethylammonium chloride, tetra-n-butylammonium chloride, tetramethylammonium(1,1,1,3,3,3-hexafluoro-2-methyl-2-propoxide), tetra-n-butylammonium(1,1,1,3,3,3-hexafluoro-2-methyl-2-propoxide), tetramethylammonium(2,6-dimethylphenoxide), tetra-n-butylammonium(2,6-dimethylphenoxide), imidazolium chloride, imidazolium(2,6-dimethylphenoxide), imidazolium(1,1,1,3,3,3-hexafluoro-2-methyl-2-propoxide), pyrrolidinium chloride, pyrrolidinium(2,6-dimethylphenoxide), tetramethylphosphonium chloride, and tetra-n-butylphosphonium chloride.

According to the method of producing the transition metal carbene complex of the disclosure, by mixing together the transition metal carbene complex represented by general formula (2) above, which has been conventionally used as a metathesis catalyst, and the onium salt represented by general formula (3) above (an ammonium salt or a phosphonium salty solvent, the intended transition metal carbene complex of the disclosure can be obtained.

Here, how the transition metal carbene complex of the disclosure can be obtained by mixing together the conventional transition metal carbene complex represented by general formula (2) and the onium salt represented by general formula (3) has yet to be revealed. However, such a mechanism is presumed as follows: When the central-metal atom M is a tungsten atom, the anion $X^-$ of the onium salt forms a highly-covalent ionic bond with highly Lewis-acidic tungsten, and the negative charge of the anion $X^-$ is delocalized over the entire molecule. This forms an onium salt complex of "ate" type to provide the transition metal carbene complex of the disclosure. On the other hand, when the central-metal atom M is a molybdenum atom, it is also presumed, similarly to the case of tungsten, that the moderate Lewis acidity of molybdenum and the stability of the onium salt would allow formation of an onium salt complex of "ate" type. Note that the reaction is not a concerted reaction between the onium salt and the central-metal atom M but is a, reaction between the anion of the onium salt and the central-metal atom M. For this, although the kind of $R^4$, $R^5$, $R^6$, and $R^7$ selected in the onium salt affects the solubility of the onium salt to a solvent, presumably, it would hardly affect the reaction with the central-metal atom M of the conventional transition metal carbene complex.

The solvent used to obtain the transition metal carbene complex of the disclosure may be any solvent that can dissolve or allows dispersion of the transition metal carbene complex and the opium salt but does not affect the reaction. However, an organic solvent is preferably used as a solvent. Specific examples usable as the organic solvent include aromatic hydrocarbons, such as benzene, toluene, and xylene; halogenated aliphatic hydrocarbons, such as dichloromethane, chloroform, 1,2-dichloroethane; halogenated aromatic hydrocarbons, such as chlorobenzene and dichlorobenzene; nitrogen-containing hydrocarbons, such as nitromethane, nitrobenzene, and acetonitrile; ethers, such as diethyl ether and tetrahydrofuran; aliphatic hydrocarbons, such as pentane, hexane, and heptane; and alicyclic hydrocarbons, such as cyclohexane, methylcyclohexane, decahydronaphthalene, bicycloheptane, tricyclodecane, and cyclooctane. Of these, halogenated aliphatic hydrocarbons are preferably used. The concentration of each component in an organic solvent is not limited in particular, and the components can be mixed in any order. When mixing together the transition metal carbene complex and the onium salt, it is preferred that no other component that may have any involvement in the reaction of the transition metal carbene complex with the onium salt be added to the solvent.

When the transition metal carbene complex represented by general formula (2) and the onium salt represented by general formula (3) are mixed together in a solvent, the ratio of each component is not limited in particular. However, the ratio of the onium salt represented by general formula (3) to the transition metal carbene complex represented by general formula (2) (i.e., onium salt represented by general formula (3)/transition metal carbene complex represented by general formula (2)) is preferably 1:1 to 100:1, more preferably 1:1 to 10:1, in a molar ratio. If the ratio is too low, the generation efficiency of the transition metal carbene complex represented by general formula (1) may become insufficient. If the ratio is too high, the intended transition metal carbene complex may not be readily separated from the opium salt represented by general formula (3) (i.e., unreacted onium salt).

The transition metal carbene complex represented by general formula (2) and the onium salt represented by general formula (3) may be mixed in a solvent at any temperature. However, it is usually selected from a range of −100° C. to 150° C., preferably from a range of −80° C. to 80° C. The mixing time is also not limited in particular, but is usually selected between 10 seconds to 24 hours.

The transition metal carbene complex represented by general formula (1) obtained by mixing together the transition metal carbene complex represented by general formula (2) and the onium salt represented by general formula (3) in a solvent can be collected for example by distilling off the solvent used for the mixing.

For example, the transition metal carbene complex of the disclosure obtained as above has significantly improved stability in an as compared with the molybdenum carbene complex or the tungsten carbene complex (i.e., the transition metal carbene complex represented by general formula (2)), which is conventionally used as a metathesis catalyst. Further, the transition metal carbene complex of the disclosure is usable as a metathesis catalyst similarly to the molybdenum carbene complex or the tungsten carbene complex conventionally used as a metathesis catalyst, and can offer high catalytic activity and stereospecificity of metathesis reaction, which are unique to molybdenum carbene complexes and tungsten carbene complexes. Therefore, the transition metal carbene complex of the disclosure is useful as a metathesis catalyst that is improved in handleability, which is a weak point of the conventional molybdenum carbene complexes and the tungsten carbene complexes, and allows stereoselective metathesis reactions such as an asymmetric olefin metathesis reaction and stereoregularity-controlling ring-opening polymerization of cyclic olefin, which are not readily achieved with ruthenium carbene complexes.

EXAMPLES

Hereinafter, the disclosed product and method will be more specifically described with reference to examples and comparative examples. Note that "%" used in the examples is by weight unless otherwise specified.

Each measurement and evaluation was performed in the following way.

(1) NMR Measurement

A nuclear magnetic resonator ("JNM-EX400WB spectrometer" manufactured by JEOL) was used to perform the measurement. The solvent used will be identified in each example. $^1$H-NMR measurement was performed at a frequency of 399.65 MHz and $^{13}$C-NMR measurement was performed at a frequency of 100.40 MHz.

(2) Evaluation of Stability of Complex

To perform the evaluation, 0.4 g of sample complex was added to 10 g of chloroform and stirred to make a uniform solution. Then, within a constant temperature and humidity box adjusted to an air temperature of 22° C. and a humidity of 50%, the solution was exposed to an atmosphere, and the change in the color of the solution was observed for 60 minutes to evaluate the stability of the complex.

(3) Cis/Trans Ratio of Ring-Opened Polymer

Using chloroform-d Or orthodichlorobenzene-$d_4$ as a solvent, $^1$H-NMR measurement of a ring-opened polymer was performed, and based on the signal strength ratio of an allyl hydrogen atom, the cis/trans ratio of the ring-opened polymer was determined.

(4) Number-Average Molecular Weight of Ring-Opened Polymer

Using chloroform-d or orthodichlorohenzene-$d_4$ as a solvent, $^1$H-NMR measurement of a ring-opened polymer was performed, and the ratio of the number of hydrogen atoms present at the terminals of the polymer chain to the number of hydrogen atoms present at locations other than the terminals of the polymer chain was obtained. Based on the ratio, the number-average molecular weight of the ring-opened polymer was calculated.

(5) Hydrogenated Percentage of Ring-Opened Polymer in Hydrogenation Reaction

Using orthodichlorobenzene-$d_4$ as a solvent. $^1$H-NMR measurement of a hydrogenated ring-opened polymer was performed at 150° C., and based on the result, hydrogenated percentage of the ring-opened polymer was obtained.

(6) Melting Point of Hydrogenated Ring-Opened Polymer

Using a differential scanning calorimeter, the measurement was performed by increasing the temperature at a rate of 10° C./min.

(7) Ratio of Mesa Dyad/Racemo Dyad of Hydrogenated Ring-Opened Polymer

Using orthodichlorobenzene-$d_4$ as a solvent, $^{13}$C-NMR measurement of a hydrogenated ring-opened polymer was performed at 150° C. Based on the strength ratio of a meso dyad-derived signal of 43.35 ppm to a racemo dyad-derived signal of 43.43 ppm, the ratio of meso dyad to racemo dyad was determined.

Example 1

Synthesis and Stability Evaluation of (tetra-n-butylammonium)[(2,6-diisopropylphenylimide){3,3'-di(t-butyl)-5,5',6,6'-tetramethyl-2,2'-biphenoxy}neophylidenemolybdenum(VI) chloride]

To a glass reactor equipped with a stirrer containing 10 mL of dichloromethane, 0.257 g of (2,6-diisopropylphenylimide){3,3'-di(t-butyl)-5,5',6,6'-tetramethyl-2,2'-biphenoxy}neophylidenemolybdenum(VI) was added and stirred to be dissolved to prepare a solution. To the solution, 0.477 g (5 eq.) of tetra-n-butylammonium chloride dissolved in 10 mL of dichloromethane was further added. After this addition, the solution whose color had been red was turned into a solution whose color is pale red. Subsequently, keeping 20° C., the solution in the reactor was stirred over 18 hours. After the 18-hour stirring, dichloromethane was distilled off from the solution. Then, a pale red solid was obtained in a yield of 95%. The solid obtained was readily soluble in chloroform, dichloromethane, diethyl ether, tetrahydrofuran, and toluene; and was less soluble in hexane. Further, the solid obtained was added to an organic solvent, which is a poor solvent for one of tetra-n-butylammonium chloride and (2,6-diisopropylphenylimide){3,3'-di(t-butyl)-5,5',6,6'-tetramethyl-2,2'-biphenoxy}neophylidenemolybdenum but is a good solvent for the other of them. Neither of the components was separated. Thus, completion of the reaction or interaction between the components was suggested. In addition, the solid obtained was subjected to $^1$H-NMR measurement (solvent: CDCl$_3$), and an α-proton peak of alkylidene was observed at 13.3 ppm. This is considered to be an α-proton peak of alkylidene of (2,6-diisopropylphenylimide){3,3'-di(t-butyl)-5,5',6,6'-tetramethyl-2,2'-biphenoxy}neophylidenemolybdenum(VI), which is observed at 10.6 ppm, shifted to a lower magnetic field side. Given the above, the pale red solid obtained can be identified as (tetra-n-butylammonium)[(2,6-diisopropylphenylimide){3,3'-di(t-butyl)-5,5,6,6'-tetramethyl-2,2'-biphenoxy}neophylidenemolybdenum(VI) chloride]. The pale red solid obtained was then evaluated for the stability of the complex. No change was observed for 60 minutes, and the complex was relatively stable.

Example 2

Synthesis and Stability Evaluation of (tetra-n-butylammonium)[(2,6-diisopropylphenylimide){bis(1,1,1,3,3,3-hexafluoro-2-methyl-2-propoxy)}neophylidenemolybdenum(VI) chloride]

To a glass reactor equipped with a stirrer containing 10 mL of dichloromethane, 0.230 g of (2,6-diisopropylphenylimide){bis(1,1,1,3,3,3-hexafluoro-2-methyl-2-propoxy)}neophylidenemolybdenum(VI) was added and stirred to be dissolved to prepared a solution to the solution, 0.0835 g. (1 eq.) of tetra-n-butylammonium chloride dissolved in 10 mL of dichloromethane was further added. After this addition, the solution whose color had been dark yellow was turned into a solution whose color is pale yellow. Subsequently, keeping 20° C., the solution in the reactor was stirred over 18 hours. After the 18-hour stirring, the solvent was distilled off from the solution. Then, a pale yellow solid was obtained in a yield of 90%. The solid obtained was readily soluble in chloroform, dichloromethane, diethyl ether, tetrahydrofuran, and toluene; and was slightly soluble in hexane. Further, the solid obtained was added to an organic solvent, which is a poor solvent for one of tetra-n-butylammonium chloride and 2,6-diisopropylphenylimide){bis(1,1,1,3,3,3-hexafluoro-2-methyl-2-propoxy)}neophylidenemolybdenum(VI) but is a good solvent for the other of them. Neither of the components was separated. Thus, completion of the reaction or interaction between the components was suggested. In addition, the solid obtained was subjected to $^1$H-NMR measurement (solvent: CDCl$_3$), and an α-proton peak of alkylidene was observed at 14.1 ppm. This is considered to be an α-proton peak of alkylidene of (2,6-diisopropylphenylimide){bis(1,1,1,3,3,3-hexafluoro-2-methyl-2-propoxy)}neophylidenemolybdenum(VI), which is observed at 12.1 ppm, shifted to a lower magnetic field side. Given the above, the pale yellow solid obtained can be identified as (tetra-n-butylammonium)[(2,6-diisopropylphenylimide){bis(1,1,1,3,3,3-hexafluoro-2-methyl-2-propoxy)}neophylidenemolybdenum(VI) chloride]. The pale yellow solid obtained was then evaluated for the stability of the complex. No change was observed for 60 minutes, and the complex was relatively stable.

Example 3

Synthesis and Stability Evaluation of (tetra-n-butylammonium)[(2,6-diisopropylphenylimide){tris(1,1,1,3,3,3-hexafluoro-2-methyl-2-propoxy)}neophylidenemolybdenum(VI)])

To a glass reactor equipped with a stirrer containing 10 mL of dichloromethane, 0.351 g of (2,6-diisopropylphenylimide){bis(1,1,1,3,3,3-hexafluoro-2-methyl-2-propoxy)}neophylidenemolybdenum(VI) was added and stirred to be dissolved to prepare a solution. To the solution, 0.195 g (1 eq.) of tetra-n-butylammonium (1,1,1,3,3,3-hexafluoro-2-methyl-2-propoxide) dispersed in 10 mL of mixed solvent of dichloromethane/diethyl ether (volume ratio 1:1) was further added. After this addition, the solution whose color had been dark yellow was turned into a solution whose color is pale yellow. Subsequently, keeping 20° C., the solution in the reactor was stirred over 18 hours. After the 18-hour stirring, the solvent was distilled off from the solution. Then, a pale yellow solid was obtained in a yield of 90%. The solid obtained was readily soluble in chloroform, dichloromethane, diethyl ether, tetrahydrofuran, and toluene; and was soluble in hexane. Further, the solid obtained was added to an organic solvent, which is a poor solvent for one of tetra-n-butylammonium (1,1,1,3,3,3-hexafluoro-2-methyl-2-propoxide) and 2,6-diisopropylphenylimide) {bis(1,1,1,3,3,3-hexafluoro-2-methyl-2-propoxy)}neophylidenemolybdenum(VI) but is a good solvent for the other of them. Neither of the components was separated. Thus, completion of the reaction or interaction between the components was suggested. In addition, the solid obtained was subjected to $^1$H-NMR measurement (solvent: C$_6$D$_6$), and an α-proton peak of alkylidene was observed at 13.8 ppm. This is considered to be an α-proton peak of alkylidene of (2,6-diisopropylphenylimide){bis(1,1,1,3,3,3-hexafluoro-2-methyl-2-propoxy)}neophylidenemolybdenum(VI), which is observed at 12.2 ppm, shifted to a lower magnetic field side. Given the above, the pale yellow solid obtained can be identified as (tetra-n-butylammonium)[(2,6-diisopropylphenylimide){tris(1,1,1,3,3,3-hexafluoro-2-methyl-2-propoxy)} neophylidenemolybdenum(VI)]. The pale yellow solid obtained was then evaluated for the stability of the complex. No change was observed for 60 minutes, and the complex was relatively stable. Note here that $^1$H-NMR spectral data of the obtained (tetra-n-butylammonium)[(2,6-diisopropylphenylimide){tris(1,1,1,3,3,3-hexafluoro-2-methyl-2-propoxy)}neophylidenemolybdenum(VI)] is the following: $^1$H-NMR (C$_6$D$_6$) δ13.8 (s, 1H, Mo═CH), 7.78 (d, 2H, Haryl), 7.26 (t, 2H, Haryl), 7.12 (t, 1H, Haul), 7.09 (t, 1H, Haryl), 6.96 (d, 2H, Haryl) 3.26 (sep, 2H, CH), 2.43 (brs, 8H, CH$_2$), 1.55 (brs, 8H, CH$_2$), 2.26 (s, 6H, CH$_3$), 2.06 (s, 6H, CH), 1.20 (d, 6H, CH$_3$), 0.95 (m, 8H, CH$_2$), 0.78 (t, 12H, CH$_3$)

Comparative Example 1

The stability of (2,6-diisopropylphenylimide){3,3'-di(t-butyl)-5,5',6,6'-tetramethyl-2,2'-biphenoxy}neophylidenemolybdenum(VI) was evaluated. The color of the solution was turned into black in 30 minutes. This color change suggests that the complex was decomposed by water in air. The complex was found to be relatively unstable.

Comparative Example 2

The stability of (2,6-diisopropylphenylimide){bis(1,1,1,3,3,3-hexafluoro-2-methyl-2-propoxy)}neophylidenemolybdenum(VI) was evaluated. The color of the solution was turned into black in 30 minutes. This color change suggests that the complex was decomposed by water in air. The complex was found to be relatively unstable.

Example 4

To a glass reactor equipped with a stirrer containing 3 mL of toluene, 0.0586 of (tetra-n-butylammonium)[(2,6-diisopropylphenylimide){3,3'-di(t-butyl)-5,5',6,6'-tetramethyl-2,2'-biphenoxy}neophylidenemolybdenum(VI) chloride] obtained in Example 1 was added and dissolved. Subsequently, to the toluene solution as obtained, within a constant temperature and humidity box adjusted to an air temperature of 22° C. and a humidity of 50%, 7.5 g of dicyclopentadiene, 27 g of cyclohexane, and 0.32 g of 1-hexene were added, and in an oil bath of 50° C., ring-opening polymerization reaction was performed with the reactor being prepared as an open system. After the start of the polymerization reaction, white precipitate was rapidly deposited. After two hours of reaction, a large amount of acetone was poured into the polymerization reaction solution to aggregate the precipitate. The aggregated precipitate was isolated by filtration and washed and then was dried under reduced pressure for 24 hours at 40° C. The yield of the ring-opened polymer obtained was 7.4 g, the cis/trans ratio was 90/10 (cis regularity), and the number-average molecular weight was 6,000. In addition, the melting point of the ring-opened polymer was 260° C., which was measured using the ring-opened polymer subjected to reduced-pressure drying directly as a sample. Next, to an autoclave equipped with a stirrer, 3.0 g of the obtained ring-opened polymer 47 g of cyclohexane were added. To the autoclave, a dispersion prepared by dispersing 0.00157 g of RuHCl(CO)(PPh$_3$)$_2$ as a hydrogenation catalyst in 10 mL of cyclohexane was further added, and hydrogenation reaction was performed for 8 hours at 160° C. under a hydrogen pressure of 4.0 MPa. This hydrogenation reaction solution was poured into a large amount of acetone, and the hydrogenated ring-opened polymer as generated was fully deposited to be isolated by filtration and washed and then was dried under reduced pressure for 24 hours at 40° C. The hydrogenated percentage of the hydrogenated ring-opened polymer as obtained was 99% or higher and a meso dyad/racemo dyad ratio was 95/5. In addition, the melting point of the hydrogenated ring-opened polymer was 290° C., which was measured using the hydrogenated ring-opened polymer subjected to reduced-pressure drying directly as a sample. The hydrogenated ring-opened polymer subjected to reduced-pressure drying was then heated for 10 minutes at 320° C. to be fully melted, and then was cooled to room temperature at a temperature-drop rate of 10° C./min, to be fully crystallized. The hydrogenated ring-opened polymer thus obtained was used as a sample, and the melting point of the sample measured was 2.89° C.

Comparative Example 3

To a glass reactor equipped with a stirrer containing 3 mL of toluene, 0.0429 g of (2,6-diisopropylphenylimide){3,3'-di(t-butyl)-5,5',6,6'-tetramethyl-2,2'-biphenoxy}neophylidenemolybdenum(VI) was added and dissolved. Subsequently, to the toluene solution as obtained, within a constant temperature and humidity box adjusted to an air temperature of 22° C. and a humidity of 50%, 7.5 g of dicyclopentadiene 27 g of cyclohexane, and 0.32 g of 1-hexene were added, and in an oil bath of 50° C., ring-opening polymerization reaction was performed with the reactor being prepared as an open system. After the start of the polymerization reaction, a small amount of white precipitate was deposited but shortly the generation of the precipitate stopped. After two hours of reaction, a large amount of acetone was poured into the polymerization reaction solution to aggregate the precipitate. The aggregated precipitate was isolated by filtration and washed and then was dried under reduced pressure for 24 hours at 40° C. The yield of the ring-opened polymer obtained was extremely small, which was 0.01 g.

Comparative Example 4

To a glass reactor equipped with a stirrer containing 3 mL of toluene, 0.0482 g of (1,3-bis(2,4,6-trimethylphenyl)-2-imidazolidinylidene)dichloro(phenyl-methylene)(tricyclohexylphosphine)ruthenium was added and dissolved. Subsequently, to the toluene solution as obtained, within a constant temperature and humidity box adjusted to an air temperature of 22° C. and a humidity of 50%, 7.5 g of dicyclopentadiene, 27 g of cyclohexane, and 0.32 g of 1-hexene were added, and in an oil bath of 50° C., ring-opening polymerization reaction was performed with the reactor being prepared as an open system. After the start of the polymerization reaction, the viscosity of the reaction solution gradually increased. After two hours of reaction, a large amount of acetone was poured into the polymerization reaction solution to aggregate the precipitate. The aggregated precipitate was isolated by filtration and washed and then was dried under reduced pressure for 24 hours at 40° C. The yield of the ring-opened polymer obtained was 7.5 g, and the ring-opened polymer was obtained quantitatively. The cis/trans ratio of the ring-opened polymer was 43/57, and cis/trans selectivity was hardly observed. The number-average molecular weight of the ring-opened polymer was 3,900. In addition, the glass transition point was 130° C., which was measured using the ring-opened polymer subjected to reduced-pressure drying directly as a sample, and no melting point was observed. Next, to an autoclave equipped with a stirrer, 0.3 g of the obtained ring-opened polymer and 4.7 g of cyclohexane were added. To the autoclave, a dispersion prepared by dispersing 0.000157 g of RuHCl(CO)(PPh$_3$)$_2$ as a hydrogenation catalyst in 1 mL of cyclohexane was further added, and hydrogenation reaction was performed for 8 hours at 160° C. under a hydrogen pressure of 4.0 MPa. This hydrogenation reaction solution was poured into a large amount of acetone, and the hydrogenated ring-opened polymer as generated was fully deposited to be isolated by filtration and washed and then was dried under reduced pressure for 24 hours at 40° C. The hydrogenated percentage of the hydrogenated ring-opened polymer as obtained was 99% or higher and the meso dyad/racemo dyad ratio was 67/33. In addition, the glass transition point was 98° C., which was measured using the hydrogenated ring-opened polymer subjected to reduced-pressure drying directly as a sample, and no melting point was observed.

The results of Examples 1 to 3 demonstrate that by mixing together the transition metal carbene complex represented by general formula (2) and the onium salt represented by general formula (3) in as solvent, the transition metal carbene complex represented by general formula, (1) can be obtained. Further, the comparison of the results of the stability evaluation of complexes of Examples 1 to 3 with those of the Comparative Examples 1 and 2 demonstrates that the transition metal carbene complex represented by general formula (1) is more stable in air than the conventional transition metal carbene complex represented by general formula (2). Still further, the results of Example 4 demonstrate that the transition metal carbene complex represented by general formula (1) is capable of ring-opening polymerizing dicyclopentadiene in an open system in air and is also capable of controlling stereoregularity to perform ring-opening polymerization. On the other hand, the results of Comparative Example 3 demonstrate that the transition metal carbene complex represented by general formula (2) is less stable with which polymerization is hardly possible in an open system in air. Moreover, the results of the Comparative Example 4 demonstrate that although the ruthenium carbene complex is capable of ring-opening polymerizing dicyclopentadiene in an open system in air, it can hardly control the stereoregularity.

The invention claimed is:

1. A transition metal carbene complex having the following general formula (1);

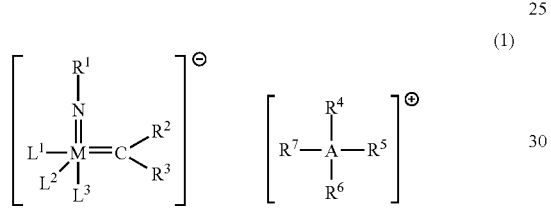

wherein in general formula (1), M is a molybdenum atom or a tungsten atom; $R^1$ is a $C_1$-$C_{20}$ alkyl group optionally having a substituent or a $C_6$-$C_{20}$ aryl group optionally having a substituent; $L^1$, $L^2$, and $L^3$ each are a ligand selected from a halogen group, an alkoxy group optionally having a substituent, and an aryloxy group optionally having a substituent, wherein $L^1$, $L^2$, and $L^3$ are the same as or different from one another, or at least two of $L^1$, $L^2$, and $L^3$ bind together to form a ring structure with M; $R^2$ and $R^3$ each are a hydrogen atom, a $C_1$-$C_{20}$ alkyl group optionally having a substituent, or a $C_6$-$C_{20}$ aryl group optionally having a substituent, wherein $R^2$ and $R^3$ are the same as or different from each other; A is a nitrogen atom or a phosphorus atom; and $R^4$, $R^5$, $R^6$, and $R^7$ each are a $C_1$-$C_{20}$ alkyl group optionally having a substituent or a $C_6$-$C_{20}$ aryl group optionally having a substituent, wherein $R^4$, $R^5$, $R^6$, and $R^7$ are the same as or different from one another, or at least two of $R^4$, $R^5$, $R^6$, and $R^7$ bind together to form a ring structure with A.

2. A method of producing the transition metal carbene complex according to claim 1, the method comprising mixing together a transition metal carbene complex having the following general formula (2) and an onium salt having the following general formula (3) in a solvent;

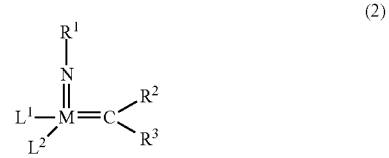

wherein in general formula (2), M is a molybdenum atom or a tungsten atom; $R^1$ is a $C_1$-$C_{20}$ alkyl group optionally having a substituent or a $C_6$-$C_{20}$ aryl group optionally having a substituent; $L^1$ and $L^2$ each are a ligand selected from a halogen group, an alkoxy group optionally having a substituent, and an aryloxy group optionally having a substituent, wherein $L^1$ and $L^2$ are the same as or different from each other, or bind together to form a ring structure with M; and $R^2$ and $R^3$ each are a hydrogen atom, a $C_1$-$C_{20}$ alkyl group optionally having a substituent, or a $C_6$-$C_{20}$ aryl group optionally having a substituent, wherein $R^2$ and $R^3$ are the same as or different from each other;

$$\begin{bmatrix} & R^4 & \\ & | & \\ R^7 - & A - & R^5 \\ & | & \\ & R^6 & \end{bmatrix}^{\oplus} X^-$$

(3)

wherein in general formula (3), A is a nitrogen atom or a phosphorus atom; $R^4$, $R^5$, $R^6$, and $R^7$ each are a $C_1$-$C_{20}$ alkyl group optionally having a substituent or a $C_6$-$C_{20}$ aryl group optionally having a substituent, wherein $R^4$, $R^5$, $R^6$, and $R^7$ are the same as or different from one another, or at least two of $R^4$, $R^5$, $R^6$, and $R^7$ bind together to form a ring structure with A; and $X^-$ is an anion selected from a halide ion, an alkoxide anion optionally having a substituent, and an aryloxide anion optionally having a substituent.

* * * * *